United States Patent [19]

Jackson

[11] Patent Number: 5,796,099
[45] Date of Patent: Aug. 18, 1998

[54] PRESSURE BASED CALIBRATION CORRECTION OF AN ION MOBILITY SPECTROMETER

[75] Inventor: Ronald A. Jackson, Mississauga, Canada

[73] Assignee: Barringer Instruments Ltd., Mississauga, Canada

[21] Appl. No.: 665,821

[22] Filed: Jun. 19, 1996

Related U.S. Application Data

[63] Continuation-in-part of Ser. No. 477,321, Jun. 7, 1995, Pat. No. 5,552,600.
[51] Int. Cl.⁶ .............. B01D 59/44; H01J 49/60
[52] U.S. Cl. .............. 250/286; 250/282
[58] Field of Search ............. 250/281, 282, 250/283, 286, 287

[56] References Cited

U.S. PATENT DOCUMENTS

| | | | |
|---|---|---|---|
| 3,812,355 | 5/1974 | Wernlund et al. | 250/283 |
| 4,777,363 | 10/1988 | Eiceman et al. | 250/286 |
| 5,294,794 | 3/1994 | Davis | 250/287 |
| 5,552,600 | 9/1996 | Davis et al. | 250/286 |

*Primary Examiner*—Bruce Anderson
*Attorney, Agent, or Firm*—David J. French

[57] ABSTRACT

The calibration of an ion mobility spectrometer is corrected for the actual operating pressure and temperature conditions within the system. An absolute pressure transducer is used to monitor absolute atmospheric pressure. This information is used in conjunction with the measured calibrant drift time to pre-determine expected drift times of target ions, compensating for any pressure and/or temperature differences from the reference conditions under which the original calibration has been carried out. This improved calibration allows the unit to be operated with a significantly lower waiting period after start-up, and also under significantly different atmospheric pressure conditions. It also improves the precision of operation of the system.

20 Claims, 4 Drawing Sheets

RATIO (Ko CAL/Ko RDX-N) VS CALIBRANT DRIFT TIME
AT VARIOUS TEMPERATURE CONDITIONS

SLOPE VERSUS STANDARD RATIO AT 105°C, 755 TORR FOR EXPLOSIVES ON THREE DETECTORS 8304, 8404, 8317

PRESSURE BASED CALIBRATION CORRECTION OF AN ION MOBILITY SPECTROMETER

This is a continuation in part of Ser. No. 08/477,321, dated Jun. 7, 1995, now U.S. Pat. No. 5,552,600.

FIELD OF THE INVENTION

This invention relates to an ion mobility spectrometry (IMS) instrument that detects chemicals present as vapours in air or other gases, or liberated as vapours from condensed phases such as particles or solutions. It particularly relates to compensating for the actual temperature and pressure conditions existing when the instrument is operated at other than standard or calibrated temperature and pressure conditions.

BACKGROUND TO THE INVENTION

Ion mobility spectrometry (IMS) instruments operate on the basis of the time taken by ionized molecules to move through a drift region containing a drift gas to a collector electrode while under the influence of an electric field. Typically the drift gas is counter-flowing to the motion of the ionized molecules. The length of time for an ion to drift to the collector is known as its drift time ($t_d$), and is a function of the size and mass of the ion, the length of the drift region ($l_d$), the strength of the electric field (E), the temperature (T) and pressure (P) in the drift region, and the composition of the drift gas. This can be represented by the following equation:

$$t_d = (l_d/EK_o)(273.5/T)(P/760) \quad (1)$$

where $K_o$, the reduced mobility constant or factor, is the ion mobility at standard temperature (273.5K) and pressure (760 torr). The reduced mobility factor is nominally a constant characteristic of a particular combination of ion and drift gas, but empirical and theoretical studies indicate that this parameter varies somewhat with temperature and pressure.

In one existing design of IMS instruments the system is operated in two modes: READY and ANALYSIS. In the READY mode the only flow in the IMS detector is a flow of drift gas which sweeps the entire length of the unit. In READY mode the IMS may be open to atmospheric pressure.

In ANALYSIS mode, a sample carrier gas also flows into the IMS detector, and both the drift and sample flows exit the detector via a suction-enhanced flow (hereafter called exhaust flow) from the exhaust port. The sample carrier gas flow (hereafter called sample flow) transports sample molecules into the IMS, where they are ionized. During ANALYSIS mode, the IMS detector may be sealed from the atmosphere but operating at atmospheric pressure.

Calibration of such a system for purposes of identifying target sample molecules by their drift times is established during READY mode by the inclusion of calibration molecules of known mass and composition (hereafter called the calibrant) in the drift flow. In the IMS detector, the calibrant (s) are ionized after they have traversed the drift region, and travel back through the drift region to a collector electrode while under the influence of the electric field. The time taken by calibrant ions to traverse the drift region and reach the collector is called the calibrant drift time, $t_d^{cal}$. From equation (1), the ratio of sample ion drift time to calibrant ion drift time is equal to the inverse ratio of their characteristic, and nominally constant reduced mobility constants, viz:

$$\frac{t_d^{sam}}{t_d^{cal}} = \frac{K_o^{cal}}{K_o^{sam}} \quad (2)$$

In the existing dual-mode system, after instrument start-up, the system searches in a programmed drift time window in the time domain to locate the calibrant ion signal and to determine its precise drift time. However, during instrument warm-up, while the system is rising to the elevated temperature at which the desorber, sample inlet, and drift tube normally operate, the calibrant drift time is changing considerably (decreasing with increasing temperature) due to the temperature changes occurring before temperature equilibrium is achieved. In addition, the pressure affects the calibrant drift time (higher pressure leads to longer drift time). For these reasons, the existing, prior art drift time window programmed for calibrant recognition is rather large and less discriminating.

When the calibrant has been recognized, and its drift time determined, the system uses that drift time and the predetermined sample/calibrant ratios of reduced mobilities to calculate the expected drift times of the target ions. This approach assumes that the reduced mobility ratios of equation (2) are substantially constant over a wide temperature and pressure range, which in turn assumes that either individual reduced mobilities do not change with temperature and pressure, or that the reduced mobilities of sample and calibrant ions change to the same proportionate extent. However, the effects of both temperature and pressure on drift times are of a complex nature and changes in these conditions may result in variable sample/calibrant drift time ratios. Consequently, the existing dual mode system can only operate reliably when its temperature has stabilized, and the ambient pressure is at or close to the pressure at which it was calibrated in the factory, typically at standard pressure and temperature.

In addition, a relatively large "error window" around each calculated target ion drift time is provided in order to compensate for errors in the calculation of these drift times, particularly when operated at temperatures and pressures that differ from the original calibration conditions. For example, operating the system at pressures that are encountered at significantly higher altitudes requires a complete re-calibration of the system. Also, unstable and differing temperatures will lead to reduced detection ability, missing of peaks, and higher false alarm rates, since the expected drift times of target ions cannot be calculated exactly from the simple sample/calibrant drift time ratio approach.

In such a system local temperatures may vary significantly within the drift region. Typically, for example, the sample gas portion of the system is operated at a higher temperature than the drift region, producing a tendency for a temperature gradient to be maintained across the drift region. However, it is a premise of the invention which follows that the various temperatures that can occur within the drift region may be treated as being equivalent to a given fixed temperature state, and such region can be described as having a "temperature condition" rather than a specific temperature.

The existing prior art, dual mode system uses a temperature sensor that delivers some data on the temperature within the drift tube. This sensor is mounted outside the actual drift tube, close to the drift tube heater, and separated from the actual drift region by the metal drift tube housing. Consequently, the temperature value delivered by such sensor can only approximate the actual temperature condition within the tube.

Due to the high electric field and electrical non-conductivity requirements inside the drift tube, it is not practical to place a sensor within the drift tube. Therefore, significant deviation may exist between the sensed and the actual temperature condition, and the sensor may indicate that the drift tube has reached its pre-programmed temperature state when in fact it has not.

The problem of compensating in an IMS device for changes in pressure or temperature within the system is addressed in U.S. Pat. No. 5,294,794. In this reference the measured value of the drift time of a selected calibrant ion species (said to be governed by the temperature and pressure within the system) is utilized to vary the field gradient in the drift region, and so adjust the transit time of other ionic species to their expected values. This is said to be effective notwithstanding deviations in the pressure and temperature within the system. This is essentially a feedback system which changes the field conditions, allowing standard, fixed procedures to be applied to discriminate between ion species. This prior art procedure does not, however, distinguish between changes due to variations in pressure or temperature individually. Instead the drift time of the selected ion species is used to determine the density of the drift gas, without distinguishing as to the source of variations in the measured gas density.

The objective of the present invention, described hereafter, is to allow an IMS system to automatically make corrections for the actual temperature condition within the system based on ambient pressure readings and calibrant drift time measurements. This will allow use of narrower target ion drift time error ranges in the detection windows resulting in improved detection ability and lower false alarm rates. It will also allow reduced warm-up periods, due to the ability of the system to accommodate different temperature conditions and correct for them. And it will allow the system to compensate for variations in ambient pressure, as may be encountered in operating the system at differing altitudes.

The invention in its general form will first be described, and then its implementation in terms of specific embodiments will be detailed with reference to drawings following hereafter. These embodiments are intended to demonstrate the principle of the invention, and the manner of its implementation. The invention in its broadest and more specific forms will then be further described and defined, in each of the individual claims which conclude this Specification.

SUMMARY OF THE INVENTION

It is a premise of the invention herein that, once the ambient pressure in the drift region is known, the calibrant drift time in a dual mode IMS system can be used not only to correct for the actual pressure at which the system is operating but also to calculate the temperature condition within the ion mobility spectrometer if all other factors such as length of drift tube, and electric field strength remain constant. This temperature condition value can then be used to correct the calculation of the expected drift times of target sample ions, based on prior target ion drift times established under known pressure and temperature conditions.

The invention applies to an ion mobility spectrometer that operates on the basis of making reference to pre-established, anticipated drift times of target ions in order to detect such ions. More specifically, the invention provides a pressure sensing means which measures the atmospheric pressure in absolute terms, and a detection control means that adjusts the anticipated drift time values for target sample ions in accordance with the measured atmospheric pressure. The invention further comprises a means of measuring the temperature condition within the drift region based on measuring the drift time experienced by calibrant ions. The anticipated drift time values for target sample ions are then further adjusted in accordance with this temperature condition to establish final corrected values for detection of target sample ions.

Thus, once the operating pressure within the system has been established, the controller within the system derives from the measured calibrant drift time and the pressure information provided by the absolute pressure sensor, a correction value to allow for the temperature condition within the drift region. This value may be used to re-calculate the expected drift times of target sample ions that may be present in ANALYSIS mode. One way this may be effected is by use of look-up tables generated from prior measurements. Alternately, an algorithm may be used to calculate the expected target ion drift times according to a formula established from prior measurements.

This feature of the invention permits the system to be operated during the warm-up phase, before the temperature (s) within the drift region have stabilized, reducing the waiting period for users. In addition, the invention allows the system to use smaller target ion drift time windows, resulting in better detection ability, and lower false alarm rates. Also, the invention permits the operation of the system at pressures significantly different from the atmospheric pressure at which the system has been originally calibrated, without the need for re-calibration.

The foregoing summarizes the principal features of the invention, and some of its optional aspects. The invention may be further understood by the description of the preferred embodiments, in conjunction with the drawings, which now follow.

DESCRIPTION OF THE PREFERRED EMBODIMENT

Figure 1:
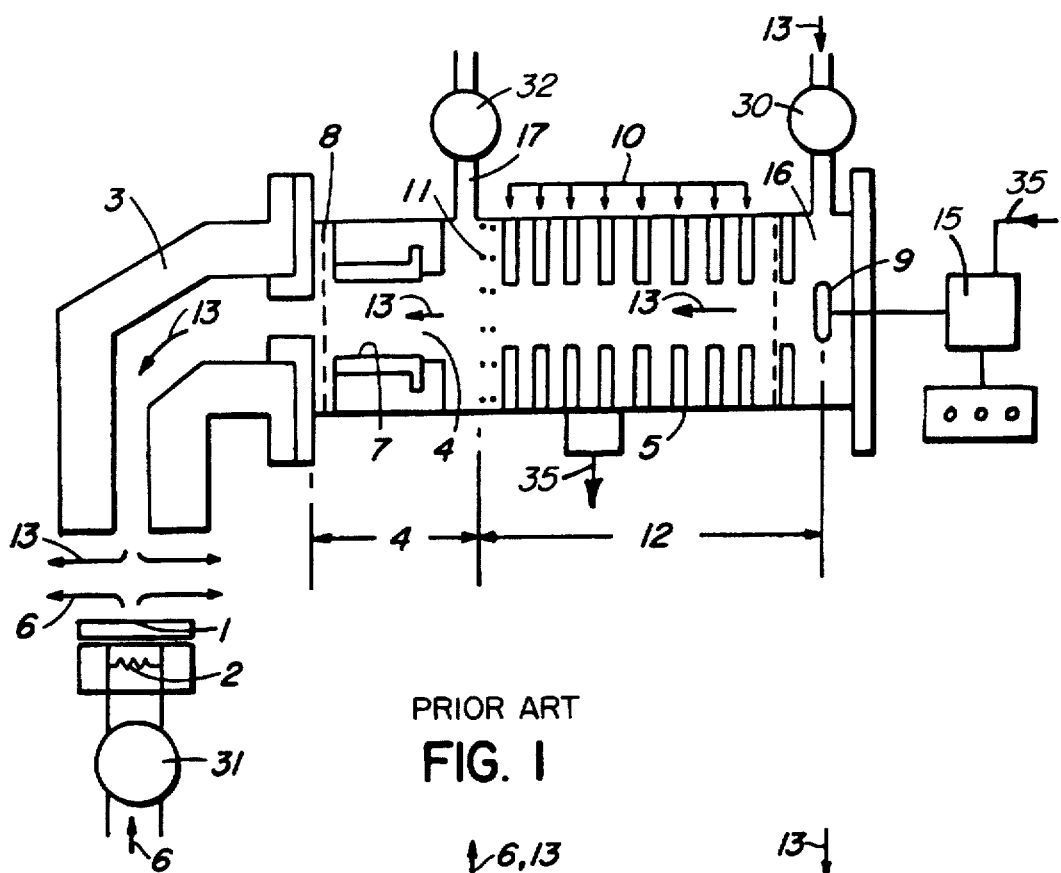
FIG. 1 is a schematic of the prior art IMS detector, open to the atmosphere in READY mode, before and between analyses. It is during this time that the calibrant drift time is measured.
Figure 2:
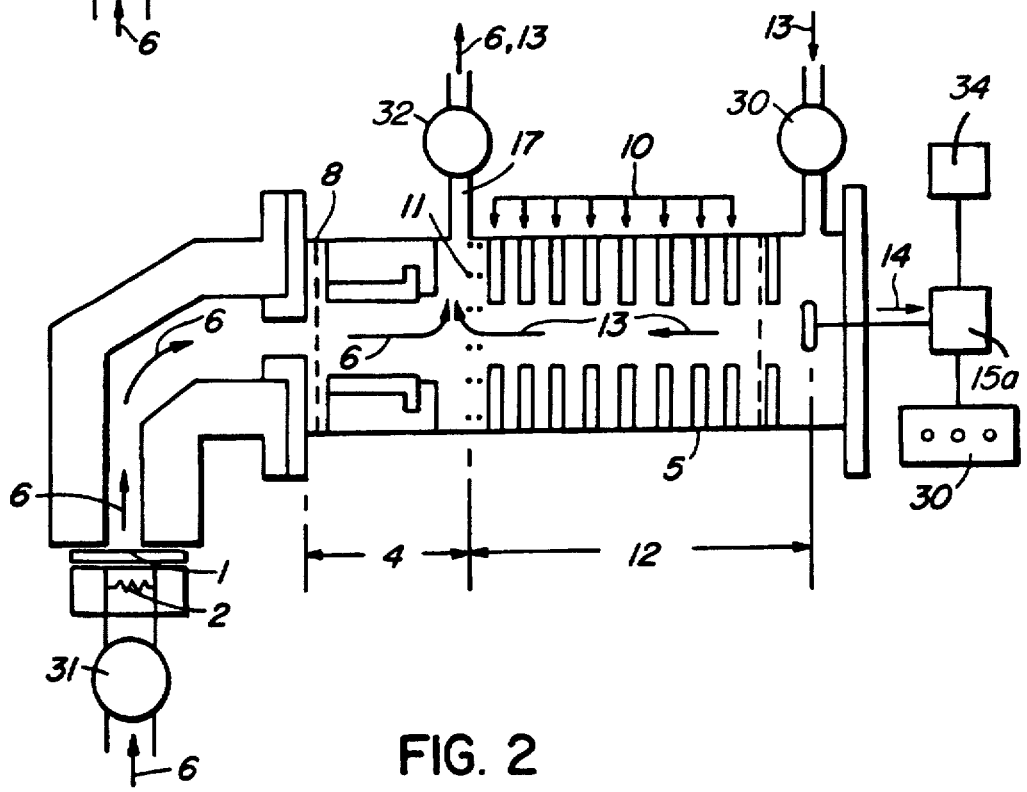
FIG. 2 is a schematic of instrument gas flows in the ANALYSIS mode of the prior art IMS detector of FIG. 1, operating at atmospheric pressure, during which time the sample is provided and ionized, and the presence of target analyte ions with their characteristic drift times is determined.

Certain IMS systems incorporate internal calibrant features, and rely on a transition from a calibration (or READY) mode to a sample testing (or ANALYSIS) mode. An IMS of this type is illustrated in FIGS. 1 and 2. In this case, the sample (1) consists of particles or other condensed phase from which vapours are liberated by application of heat from a desorber heater (2), with the vapours carried through a heated sample gas inlet passageway (3) to the ionization/reaction region (4) of the IMS drift tube (5) by a flow of sample carrier gas (6). Alternatively, samples already in the vapour state may be introduced in a similar fashion or by injection through a septum.

Vapours in the ionization/reaction region (4) are ionized by electrons emitted from an electron source such as $^{63}$Ni (7), and by interactions with other vapour molecules present, which may include added reactants. An electric field gradient is established between the repelling ring (8) at the entrance to the drift tube and the collector electrode (9) at the other end of the drift tube through the use of drift rings (10) in the drift region (12). Ions of appropriate polarity move to the electronic gating grid (11), which separates the ionization/reaction region (4) and the drift region (12) of the drift tube (5).

Progress of ions to the drift region is stopped by a small opposite potential at the gating grid (11). This gating grid potential is periodically reversed for short periods of time, typically 200 microseconds, during which interval a packet of ions enters the drift region (12) and moves toward the collector electrode (9) against a counterflow of drift gas (13). During this movement, the different ionic species in the packet separate, with the smaller, lighter ions reaching the collector electrode (9) ahead of larger heavier ions.

Current at the collector electrode, produced by the arrival of such ions, is measured, and may be presented as a function of time elapsed from the last gating pulse. This transit time is called drift time. Typically up to 30 milliseconds elapse between gating pulses. The collector current signals (14) are digitized in a controller system (15), with multiple scans being added together to form one analysis sample reading, typically consisting of about 20 scans. Several analysis sample readings are obtained throughout the sample desorption period of typically 5 to 10 seconds.

The flow of drift gas (13) containing trace amounts of calibrant(s) enters the drift tube (5) at the collector electrode end (16). This flow is maintained in both READY and ANALYSIS modes by valve (30). The sample carrier gas flow (6) only enters the inlet (3) and drift tube (5) through valve (31) in the ANALYSIS mode. The exhaust (suction) flow through the exhaust port (17) is only activated by valve (32) in the ANALYSIS mode. In the READY mode, the sample carrier gas flow (6) disperses into the air surrounding the desorber (2), and the exhaust port (17) is closed.

In READY mode, the drift gas containing trace amounts of calibrant(s) therefore passes through the drift tube (5). The calibrant molecules in the drift gas are ionized in the ionization/reaction region (4) and repelled towards the gating grid (11), where activation of the gating pulse will allow a packet of ions (including the calibrant(s)) to move into the drift region (12) towards the collector electrode (9).

In READY mode, once a precalibrated external drift tube temperature is measured by a temperature sensor (35), calibrant ions are regularly pulsed into the drift region (12), and the calibrant ion drift time is measured from the location of the peak of the calibrant signal in the time domain. This peak is identified as being that of the calibrant by its presence in a predetermined permissible drift time window established previously for the calibrant ion.

The actual measured calibrant drift time will vary within the permissible calibrant drift time window in accordance with the pressure and temperature condition within the drift tube (5). This calibrant drift time is subsequently used to calculate the expected drift times of the various target sample ions which may be present during a subsequent ANALYSIS mode.

Since the drift tube (5) and inlet (3) are an open system in the READY mode, the pressure within the drift tube during the READY mode is at or nearly at ambient or atmospheric level. In the new inventive arrangement an absolute pressure transducer (34) measures this pressure and provides a corresponding pressure signal to the system controller (15). Previously, the pressure has been assumed to be at or near standard atmospheric pressure.

In the ANALYSIS mode, depicted in FIG. 2, a sample (1) is placed on the desorber heater (2) at the entrance of the sample gas inlet, and the system is sealed to the entrance of the inlet passageway (3). Sample carrier gas (6) containing the thermally desorbed sample vapours flows into the ionization/reaction region (4) through the sample gas inlet (3) in a direction counter to that of the drift gas (13). At the same time, the exhaust port (17) is opened, and an externally applied suction draws the sample carrier gas (6), drift gas (13), and un-ionized sample gas (6) out by this means.

In this mode the controller (15) searches in predicted time domain detection windows for the presence or absence of detector current signals arising in the drift time intervals calculated for anticipated target ions. The predicted time domain detection windows are established by relying on the measured absolute pressure and the temperature condition values established from calibrant ion drift times measured during READY mode. The prior measurement of the calibrant ion drift time in the READY mode is thus used to establish the anticipated target ion drift time detection or search windows for various anticipated target ions.

Target ion drift times are measured from the peak current signal, surrounding a current signal having the dispersion expected for the target ion. Current signal wave forms meeting pre-established criteria are assumed to represent a "hit". The system then provides an indication for the operator that target ions have been found.

Figure 3:
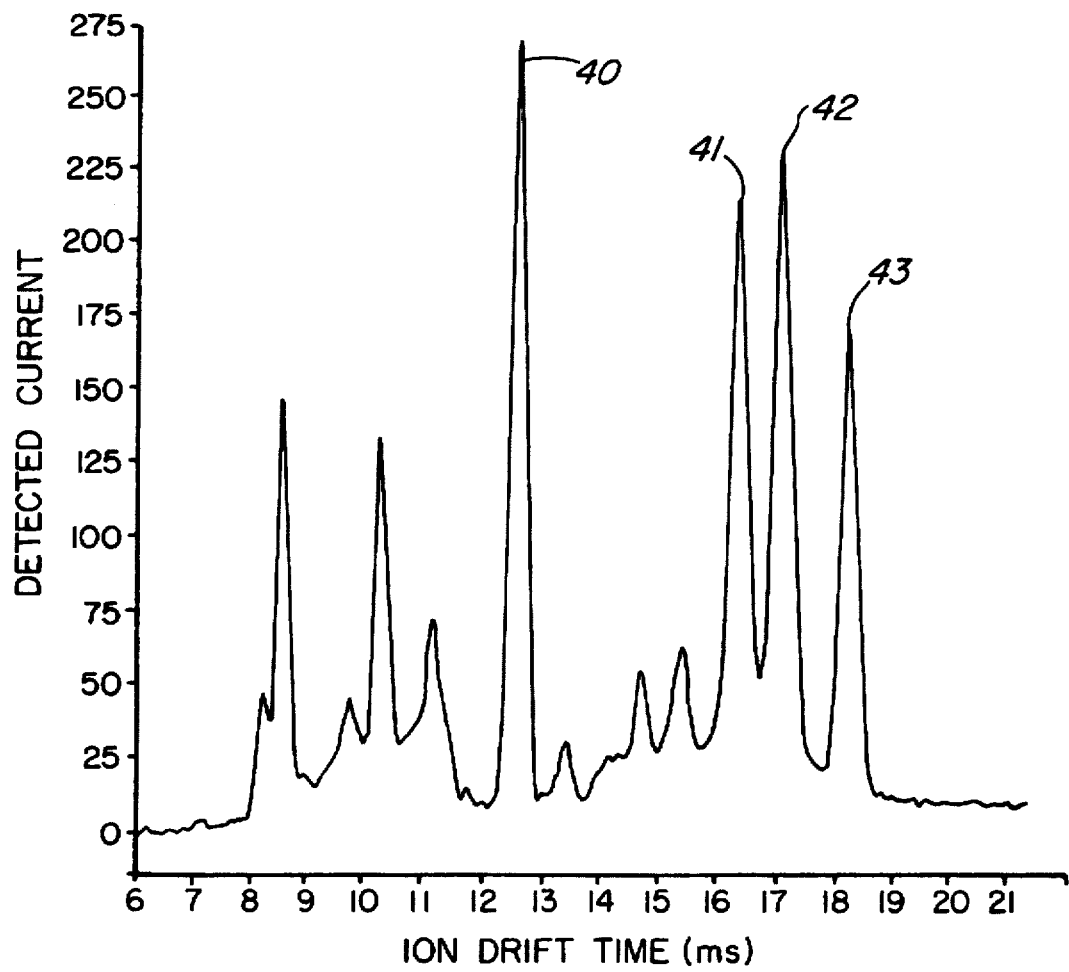
FIG. 3 is a typical prior art output from the detector of FIG. 1, showing a display of current peaks indicating drift times for analyzed sample ions.

A graphic representation of the detector signals in ANALYSIS mode with annotations interpreting the signals is shown in FIG. 3. The peak 40 is the signal created by the arrival of the calibrant ion. Peak 41 is a cluster ion of PETN (pentaerythritol tetranitrate, an explosive) and a chloride ion. Peak 42 is a cluster of PETN and a nitrate ion, and Peak 43 is a cluster of PETN and an ion derived from human finger oil, respectively. The other peaks appearing at drift times shorter than the calibrant are background signals. The ion drift times of these substances appears from the X axis scale. With changes in temperature and pressure, the depicted peaks will shift to the left or right on the X axis scale.

The procedure by which the existing system identifies target ions is as follows. Upon system start-up the system searches the calibrant search window for the appearance of a peak, once the flow rates of sample, drift, and exhaust gas have been established, the high voltage is stable, and the temperature indicators are at pre-set start-up levels. A peak detected in the time domain search window that satisfies certain pre-programmed criteria such a height and shape is recognized as the detection of a collector current signal corresponding to the calibrant ion. The instrument enters into READY mode when the calibrant ion is found and remains in READY mode as long as the drift time for the calibrant is within a predetermined range. The measured drift time for this calibrant ion is thereafter used to adjust the search window location for anticipated target ions amongst the sample ions when in ANALYSIS mode.

Due to the complex relationship existing between drift times and the temperature condition within the system, the values for target ion/calibrant ion drift time ratios will differ with the temperature condition within the drift tube (5). If the system is operated on the possibly misconceived assumption that the calibration level of temperature has been reached within the system, the analysis may miss the target ions present in the sample. However, it is a feature of the present invention that the measured drift time of the calibrant ion may also be used as a means to determine the temperature condition within the system, and to correct the position of the target ion search window in accordance with such actual temperature condition.

Additionally, without the presence of pressure compensation, instrument operation at atmospheric pressure conditions significantly different from those at the time of initial calibration will also lead to incorrectly calculated target ion drift times. Again, the expected drift times for target ions can be adjusted to correct for such pressure differentials if the actual atmospheric pressure level is measured via absolute pressure sensor (34) while the system is operating. To a first level of approximation this correction may be based on assuming a linear response to pressure variations.

A system incorporating the invention operates to determine anticipated target ion drift times as follows. Once the calibrant ion peak has been identified, its drift time is used, in conjunction with the absolute pressure information provided by the absolute pressure sensor (34), to adjust the calibration/target ion drift time ratio in accordance with the actual pressure and temperature condition within the system. Effectively, the measured calibrant ion drift time is used to determine the temperature condition within the drift tube. The pressure condition of the system is measured by the absolute pressure sensor (34) and these values are used by the controller (15a) to establish the anticipated target on drift time.

Corrected anticipated target ion drift times may be determined from the measured pressure and calibration ion drift time surrogate for the temperature condition values by using a look-up table based on prior measurements for anticipated target ions. Alternately, an algorithm established by prior measurements may be used to adjust the system in response to the pressure and temperature condition in the system.

A suitable algorithm for use with a specific pretested target ion is as follows:

$$K^1 = K^{Cal} \times cf$$

with $$\frac{1}{CF} = \frac{K^{Cal}}{K_o} + \left[ \frac{P_{Ref}}{P_{Obs}} \times D^{Cal}_{Obs} - D^{Cal}_{Ref} \right] \times [slope]$$

wherein:

$K^1$=corrected reduced mobility of target ion $K^{Cal}$=reduced mobility of calibrant at a reference calibration pressure and temperature CF=correction factor $K_o$=reduced mobility of target ion at the reference calibration pressure and temperature $P_{Ref}$=reference atmospheric pressure at which initial calibration was effected $P_{Obs}$=observed ambient atmospheric pressure $D^{Cal}_{Ref}$=reference drift time of calibrant measured at the reference pressure ($P_{Ref}$) and reference temperature ($T_{Ref}$) during initial calibration $D^{Cal}_{Obs}$=observed drift time of calibrant Slope=slope of the best-fit straight line for a data calibration function for the target ion wherein the ratio of the measured reduced mobility factor of the calibrant ion divided by the measured reduced mobility factor of the target ion is plotted as a function of the pressure-corrected calibrant drift time for changing temperature conditions in the drift tube.

Sample values for this slope parameter based on use of 4-nitrobenzonitrile as the calibrant are as follows:

| | Ion | | Slope |
|---|---|---|---|
| 1. | $NO_3$ | nitrate ion | $2.43 \times 10^{-6}$ microsec$^{-1}$ |
| 2. | TNT | trinitrotoluene | $-7.14 \times 10^{-6}$ microsec$^{-1}$ |
| 3. | RDX-C | RDX-Cl ion adduct | $-12.51 \times 10^{-6}$ microsec$^{-1}$ |
| 4. | NG-C | NG-$NO_3$ ion adduct | $-9.70 \times 10^{-6}$ microsec$^{-1}$ |
| 5. | RDX-N | RDX-$NO_3$ ion adduct | $-9.53 \times 10^{-6}$ microsec$^{-1}$ |
| 6. | NG-N | NG-$NO_3$ ion adduct | $-11.6 \times 10^{-6}$ microsec$^{-1}$ |
| 7. | PETN-C | PETN-Cl ion adduct | $-15.3 \times 10^{-6}$ microsec$^{-1}$ |
| 8. | PETN-N | PETN-$NO_3$ ion adduct | $-17.5 \times 10^{-6}$ microsec$^{-1}$ |
| 9. | RDX-D | RDX-RDX-Cl ion adduct | $-28.6 \times 10^{-6}$ microsec$^{-1}$ |

Target ions heavier than the calibrant ion have a negative slope value. Lighter ions have a positive slope value.

The listed ions are all ions that are best detected when negatively ionized. The system performs similarly with positively charged ions. A preferred calibrant ion for positively charged ions is nicotinamide.

The "slope" values for various ions were obtained from test data as follows.

Figure 4:
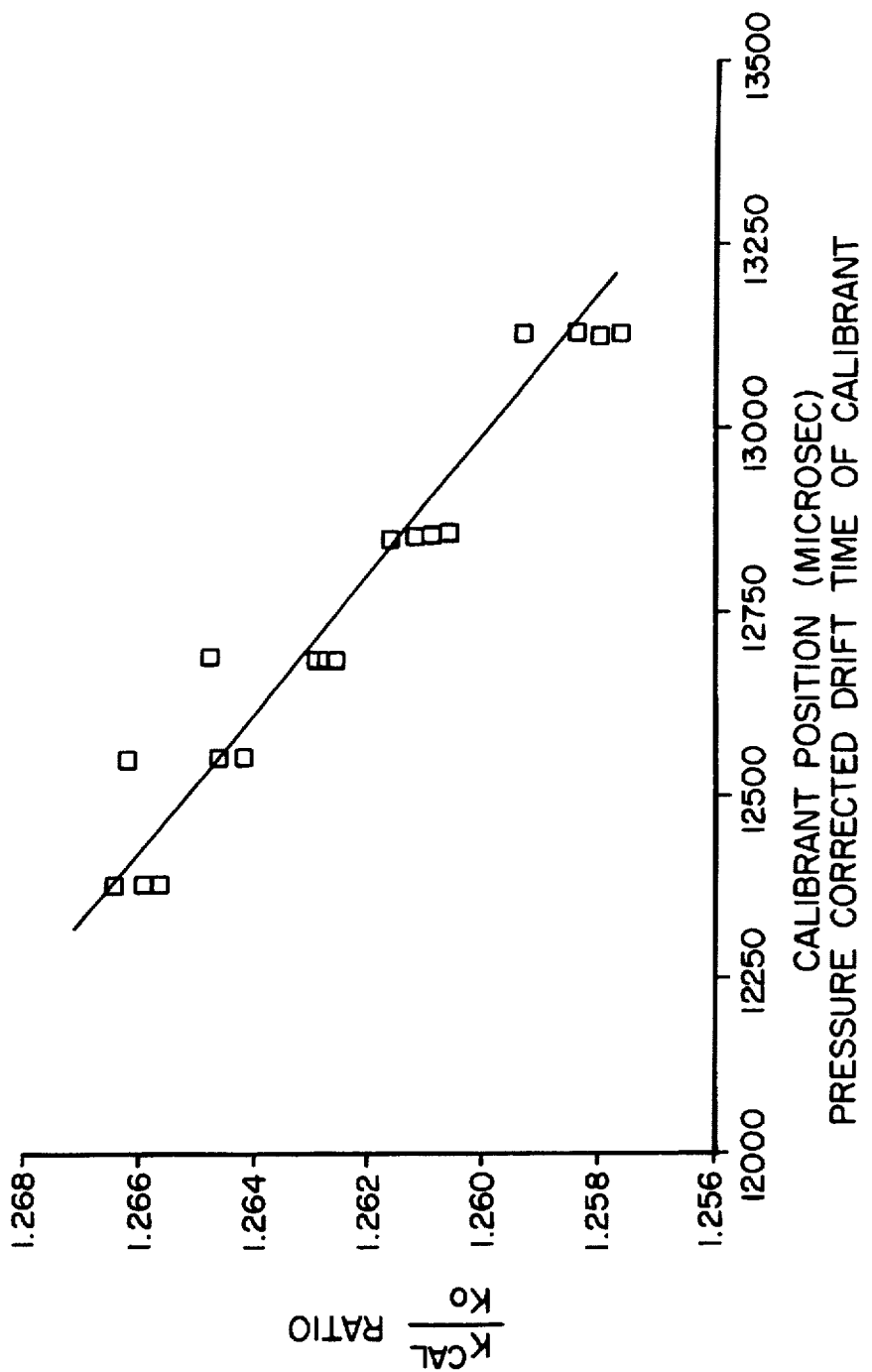
FIG. 4 shows data for the ratio of the observed reduced mobility factor for the calibrant ion divided by that of the target ion as a function of the observed, pressure-corrected drift time of the calibrant as the temperature condition of the system is varied. This data is used for entry into a correction algorithm applied in implementing the invention.

Values for the actual measured drift time for a specific target ion and a calibrant arising under varying temperature conditions were determined by running the system under a variety of different temperatures at a reference pressure. The ratio of the measured values for the drift times of the target ion and calibrant were then plotted against the corresponding pressure-corrected drift time of the calibrant for each temperature condition. The measured calibrant drift time at the measured pressure was converted to the corresponding pressure-corrected drift time at a reference pressure assuming a direct linear variation with absolute pressure. This results in a graph typically looking like FIG. 4. From this graph can be obtained a slope value (of the straight line of best fit) for the target ion that is a measure of the rate of change of the sample ion's normalized drift time (with respect to the calibrant ion) for varying temperature conditions. FIG. 4 uses $$\frac{K^{Cal}}{K_o}$$

for the "y"-axis being the ratio of the measured values for these parameters. This is substantially the same value as $$\frac{t^{tam}_d}{t^{cal}_d}$$

under similar conditions.

A generalized equation may also be developed for a variety of target ions. The slope values obtained for a variety of target ions may be entered into a second plot as Y-values where the X-values are the ratios of the measured reduced mobility values for the calibrant $K^{Cal}$ over the target ion $K_o$ at the reference temperature and pressure at which calibration is made. The results provide a graph as depicted in FIG. 5.

Figure 5:
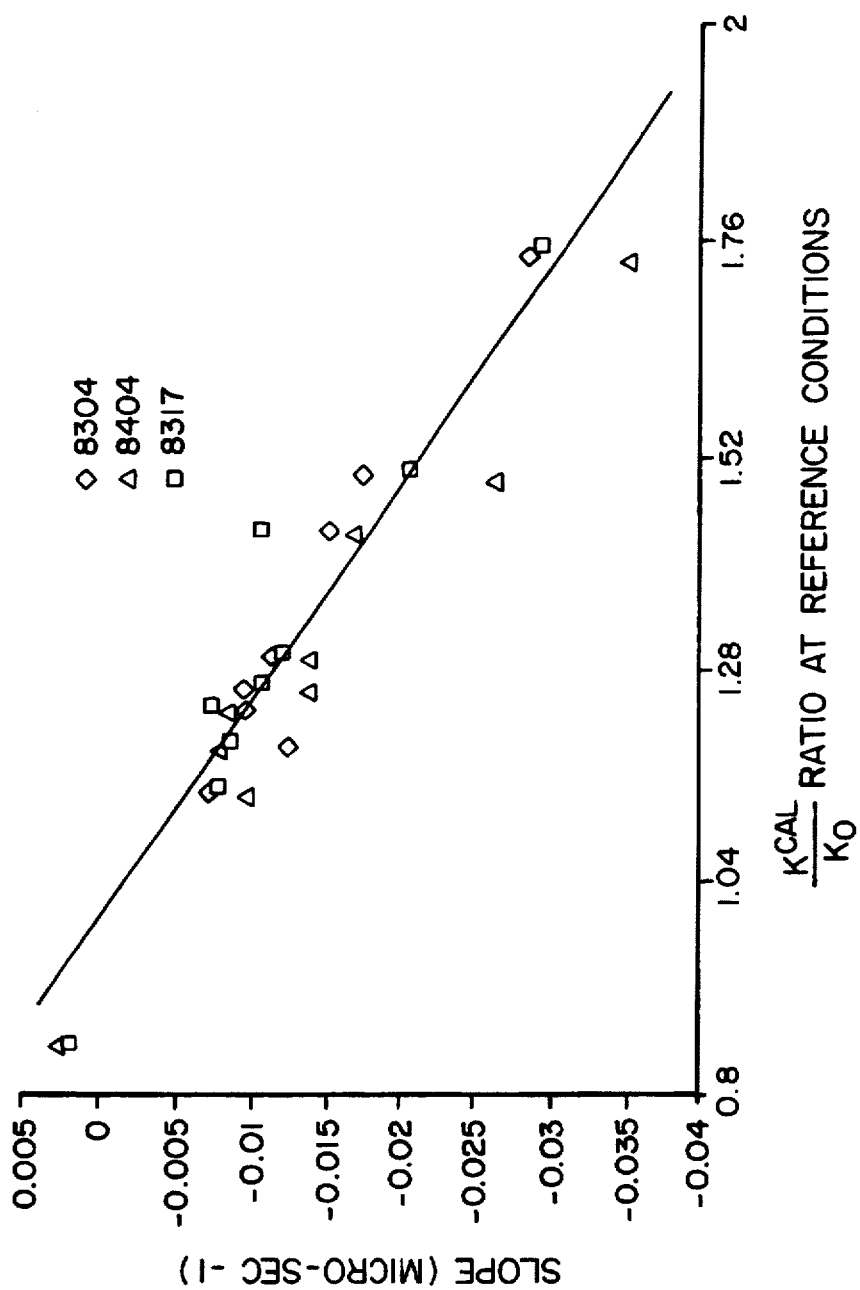
FIG. 5 shows a graph by which the slope of the straight line of best fit of the data of FIG. 4 for a series of different ions is plotted as a function of the ratio of the reduced mobility factor of the calibrant divided that of the sample ion at a reference calibration temperature, again for entry into a correction algorithm used in implementing the invention.

FIG. 5 may be used to determine the slope value for any target ion based upon knowing the standard $K_o$ value for that ion by use of the following formula:

$$\text{slope} = ROCS\left[\frac{K^{cal}}{K_o} - 1\right] + \text{intcpt}$$

Wherein the "ROCS" (Rate of Change of Slope) value is the arithmetic slope of FIG. 5.

The "intcpt" value is the Y-value that occurs for an X-value of 1 in FIG. 5. This the same point where the $K_o$ of the target ion and calibrant ion are identical. The "intcpt" would theoretically be zero in such cases, but differs from zero when the best-fit straight line of FIG. 5 is applied to target ions that differ from this equality ratio, thus being graphically removed from the X=1 position.

From measurements based on the following target ions: $NO_3$, TNT, RDX-C, RDX-N, RDX-D, NG-N, NG-C, PETN-C, PETN-N, it has been found that ROCS and intcpt values falling into the following ranges may be used in the above algorithm for negatively charged ions:

ROCS = $-20\times10^{-6}$ to $-50\times10^{-6}$ microsec$^{-1}$ (more preferably ROCS = $-34\times10^{-6}$ to $-40\times10^{-6}$ microsec$^{-1}$)

intcpt = $-2.5\times10^{-6}$ to $+0.1\times10^{-6}$ microsec$^{-1}$

Similar values for positively charged ions are as follows:

ROCS = $-45\times10^{-6}$ to $-85\times10^{-6}$ microsec$^{-1}$ (more preferably ROCS = $-65\times10^{-6}$ to $-75\times10^{-6}$ microsec$^{-1}$)

intcpt = $-10\times10^{-6}$ to $+0.1\times10^{-6}$ microsec$^{-1}$)

As the intcpt values are small relative to the ROCS values the algorithm will work adequately by using intcpt=0.

The combined algorithms allow the expected drift time of any given target ion (whose $K_o$ is known) to be calculated to a corrected value using the actual, measured calibrant drift time and the measured pressure, providing a correction for the actual temperature condition in the drift region and the ambient pressure.

The measurements and calculation of values based on the correction algorithm as indicated are carried out continuously in the READY mode during the operation of the system, making constant adjustments to the expected target ion drift times. Since the invention does not assume the existence of constant relationships between sample/calibrant drift time ratios with changes in temperature and pressure, but uses look-up tables or algorithms based on prior measurements instead to establish these ratios, the expected value for a target ion drift time is a much better approximation of the real drift time under the conditions employed. This will allow the system to operate at pressures and temperatures significantly different from equilibrium or calibrated reference values without loss of detection capacity. In particular, the system can be used during a portion of the previously unavailable warm-up time, greatly enhancing its operational availability.

In addition, the system will permit the use of narrower error windows around the expected drift times, increasing selectivity and lowering false alarm rates.

CONCLUSION

The foregoing has constituted a description of specific embodiments showing how the invention may be applied and put into use. These embodiments are only exemplary. The invention in its broadest, and more specific aspects, is further described and defined in the claims which now follow.

These claims, and the language used therein, are to be understood in terms of the variants of the invention which have been described. They are not to be restricted to such variants, but are to be read as covering the full scope of the invention as is implicit within the invention and the disclosure that has been provided herein.

The embodiments of the invention in which an exclusive property are claimed as follows:

1. An ion mobility spectrometer comprising:

(1) a drift tube having a drift gas inlet, a drift region, electronic field generation means for establishing an electrostatic field within the drift region and drift gas containing calibrant ions;

(2) a sample gas inlet for introducing sample ions into the drift tube that may include target ions;

(3) an exhaust gas outlet;

(4) pressure measurement means for measuring the absolute pressure of the drift gas in the drift region of the system;

(5) ion detection means for measuring the drift time of said calibrant ions and for detecting the presence of target ions amongst the sample ions; and (6) output means coupled to said ion detection means for providing an indication whether target ions are detected as being present in the sample gas, wherein the ion detection means provides an output indicating the presence of target ions within the sample gas based on an expected drift time for such target ions that is established by reference to the measured absolute pressure in the drift region and the temperature condition within the drift region as determined by measuring the drift time of calibration ions within the spectrometer.

2. A spectrometer as in claim 1 wherein the absolute pressure measurement and the calibrant ion drift time measurement are used by the ion detection means to calculate expected drift times of target ions, utilizing the following formula:

$$t_d = (l_d/EK^1)(273.5/T)(P/760)$$

$$K^1 = K^{Cal} \times CF$$

with $$\frac{1}{CF} = \frac{K^{Cal}}{K_o} + \left[\frac{P_{Ref}}{P_{Obs}} \times D^{Cal}_{Obs} - D^{Cal}_{Ref}\right] \times \text{slope}$$

wherein:

$t_d$ = expected drift time of the target ion $l_d$ = length of drift region

E = strength of the electric field

T = measured temperature p = measured pressure $K^1$ = corrected reduced mobility of target ion $K_{Cal}$ = reduced mobility of calibrant at a reference pressure and temperature CF = correction factor $K_o$ = reduced mobility of target ion at the reference pressure and temperature $P_{Ref}$ = reference atmospheric pressure at which initial calibration was effected $P_{Obs}$ = observed ambient atmospheric pressure $D^{Cal}_{Ref}$ = reference drift time of calibrant measured at the reference pressure (Pref) and reference temperature condition during initial calibration $D^{Cal}_{Obs}$ = observed drift time of calibrant slope=slope of the best-fit straight line for a data calibration function wherein the ratio of the measured reduced mobility factor of the calibrant ion divided by the measured reduced mobility factor of the target ion is plotted as a function of the pressure-corrected calibrant drift time for changing temperature conditions in the drift tube.

3. A spectrometer as in claim 2 wherein the slope value is determined using the following formula:

$$slope = ROCS \left[ \frac{K^{Cal}}{K_o} - 1 \right]$$

wherein:
ROCS=the rate of change of slope of the best-fit straight line for a plot of slope values for a number of target ions as a function of the ratio of the reduced mobility factor of the calibrant ion divided by the reduced mobility factor of the sample ion at the reference pressure and temperature.

4. A spectrometer as in claim 3 wherein the sample ions are negatively charged and ROCS is in the following range:

$$ROCS = -20 \times 10^{-6} \text{ to } -50 \times 10^{-6} \text{ microsec}^{-1}.$$

5. A spectrometer as in claim 3 wherein the sample ions are negatively charged and ROCS is in the following range:

$$ROCS = -34 \times 10^{-6} \text{ to } -40 \times 10^{-6} \text{ microsec}^1.$$

6. A spectrometer as in claim 3 the sample ions are positively charged and ROCS is in the following range:

$$ROCS = -45 \times 10^{-6} \text{ to } -85 \times 10^{-6} \text{ microsec}^{-1}.$$

7. A spectrometer as in claim 3 the sample ions are positively charged and ROCS is in the following range:

$$ROCS = -65 \times 10^{-6} \text{ to } -75 \times 10^{-6} \text{ microsec}^1.$$

8. A spectrometer as in claim 3 wherein the slope value is determined using the following formula:

$$slope = ROCS \left[ \frac{K^{Cal}}{K_o} - 1 \right] + intcpt$$

wherein:
intcpt=value of the best-fit straight line through the plot of slope values of multiple target ions as a function of the $K^{Cal}/K_o$ ratio for each target ion for the case where $$\frac{K^{Cal}}{K_o} = 1.$$

9. A spectrometer as in claim 8 wherein the sample ions are negatively charged and ROCS and intpct are in the following range:

$$ROCS = -20 \times 10^{-6} \text{ to } -50 \times 10^{-6} \text{ microsec}^{-1}$$

$$intcpt = -2.5 \times 10^{-6} \text{ to } +0.1 \times 10^{-6} \text{ microsec}^{-1}.$$

10. A spectrometer as in claim 8 wherein the sample ions are negatively charged and ROCS and intpct are in the following range:

$$ROCS = -34 \times 10^{-6} \text{ to } -40 \times 10^{-6} \text{ microsec}^{-1}$$

$$intcpt = -2.5 \times 10^{-6} \text{ to } 0.1 \times 10^{-6} \text{ microsec}^{-1}.$$

11. A spectrometer as in claim 8 the sample ions are positively charged and ROCS and intcpt are in the following range:

$$ROCS = -45 \times 10^{-6} \text{ to } -85 \times 10^{-6} \text{ microsec}^{-1}$$

$$intcpt = -10 \times 10^{-6} \text{ to } +0.1 \times 10^{-6} \text{ microsec}^{-1}.$$

12. A spectrometer as in claim 8 the sample ions are positively charged and ROCS and intcpt are in the following range:

$$ROCS = -65 \times 10^{-6} \text{ to } -75 \times 10^{-6} \text{ microsec}^{-1}$$

$$intcpt = -10 \times 10^{-6} \text{ to } +0.1 \times 10^{-6} \text{ microsec}^{-1}.$$

13. An ion mobility spectrometer comprising:
(1) a drift tube having a drift gas inlet, a drift region, and electronic field generation means for establishing an electrostatic field within the drift region and drift gas containing calibrant ions;
(2) a sample gas inlet for introducing sample ions into the drift tube that may include target ions;
(3) an exhaust gas outlet;
(4) pressure measurement means for measuring the absolute pressure of the drift gas in the drift region of the system;
(5) ion detection means for measuring the drift time of said calibrant and for detecting the presence of target ions amongst the sample ions; and
(6) output means coupled to said ion detection means for providing an indication whether target ions have been detected in the sample gas,
wherein the output means provides an output indicating the presence of target ions within the sample ions by detection of sample ions having predetermined target ion drift times, said predetermined target ion drift times being adjusted in response to the measured absolute pressure of the drift gas and the measured drift time of calibrant ions within the spectrometer, as determined by the ion detection means.

14. In an ion mobility spectrometer comprising:
(1) a drift tube having a drift gas inlet, a drift region, electronic field generation means for establishing an electrostatic field within the drift region and drift gas containing calibrant ions;
(2) a sample gas inlet for introducing sample ions into the drift tube that may include target ions;
(3) an exhaust gas outlet;
(4) pressure measurement means for measuring the absolute pressure of the drift gas in the drift region of the system;
(5) ion detection means for measuring the drift time of said calibrant ions and for detecting the presence of target ions amongst the sample ions based on the expected drift times of such target ions; and
(6) output means coupled to said ion detection means for providing an indication whether target ions are detected as being present in the sample gas,
the method of establishing an expected drift time for such target ions by:
(1) measuring the pressure in the drift region to obtain a pressure value for the system;
(2) measuring the drift time of the calibrant ion to obtain the calibrant drift time;
(3) utilizing such pressure value and calibrant drift time to establish the expected drift time of a possible target ion; and (4) providing an output indication that target ions are present in the sample gas when target ions having the expected drift time are detected by the ion detection means.

15. A method as in claim 14 wherein the absolute pressure measurement and the calibrant ion drift time measurement are used by the ion detection means to calculate expected drift times of target ions, utilizing the following formula:

$$t_d = (l_d/EK^1)(273.5/T)(P/760)$$

$$K^1 = K^{Cal} \times CF$$

with $$\frac{1}{CF} = \frac{K^{Cal}}{K_o} + \left[ \frac{P_{Ref}}{P_{Obs}} \times D^{Cal}_{Obs} - D^{Cal}_{Ref} \right] \times \text{slope}$$

$t_d$=expected drift time of the target ion
$l_d$=length of drift region
E=strength of the electric field
T=measured temperature
P=measured pressure
wherein:
$K^1$=corrected reduced mobility of target ion
$K^{Cal}$=reduced mobility of calibrant at a reference pressure and temperature
CF=correction factor
$K_o$=uncorrected reduced mobility of target ion at the reference pressure and temperature
$P_{Ref}$=reference atmospheric pressure at which initial calibration was effected
$P_{Obs}$=observed ambient atmospheric pressure
$D^{Cal}_{Ref}$=reference drift time of calibrant measured at the reference pressure (Pref) and reference temperature condition during initial calibration
$D^{Cal}_{Obs}$=observed drift time of calibrant slope=slope of the best-fit straight line for a data calibration function wherein the ratio of the measured reduced mobility factor of the calibration ion divided by the measured reduced mobility factor of the target ion is plotted as a function of the pressure-corrected calibrant drift time for changing temperature conditions in the drift tube.

16. A method as in claim 15 wherein the slope value is determined using the following formula:

$$\text{slope} = ROCS \left[ \frac{K^{Cal}}{K_o} - 1 \right]$$

wherein:

ROCS=the rate of change of slope of the best-fit straight line for a plot of slope values for a number of target ion as a function of the observed $\overline{K^{Cal}/K_o}$ ratio at reference conditions.

17. A method as in claim 16 wherein the sample ions are negatively charged and ROCS is in the following range:

$$ROCS = -20 \times 10^{-6} \text{ to } -50 \times 10^{-6} \text{ microsec}^{-1}.$$

18. A method as in claim 16 wherein the sample ions are negatively charged and ROCS is in the following range:

$$ROCS = -34 \times 10^{-6} \text{ to } -40 \times 10^{-6} \text{ microsec}^{-1}.$$

19. A method as in claim 16 wherein the sample ions are positively charged and ROCS is in the following range:

$$ROCS = -45 \times 10^{-6} \text{ to } -85 \times 10^{-6} \text{ microsec}^{-1}.$$

20. A method as in claim 16 wherein the sample ions are positively charged and ROCS is in the following range:

$$ROCS = -65 \times 10^{-6} \text{ to } -75 \times 10^{-6} \text{ microsec}^{-1}.$$

* * * * *